US006946173B2

United States Patent
Lim et al.

(10) Patent No.: US 6,946,173 B2
(45) Date of Patent: Sep. 20, 2005

(54) CATHETER BALLOON FORMED OF EPTFE AND A DIENE POLYMER

(75) Inventors: Florencia Lim, Union City, CA (US); Chi Le Long, San Jose, CA (US); Charles D. Claude, Santa Clara, CA (US); Jeong S. Lee, Diamond Bar, CA (US); Srinivasan Sridharan, Morgan Hill, CA (US); Fernando Gonzalez, Campbell, CA (US); Edwin Wang, Tustin, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/103,274

(22) Filed: Mar. 21, 2002

(65) Prior Publication Data

US 2003/0180488 A1 Sep. 25, 2003

(51) Int. Cl.$^7$ ............. B32B 1/08; A61M 25/10; A61M 29/00
(52) U.S. Cl. ............. 428/35.2; 428/34.1; 428/35.7; 428/36.5; 428/36.8; 428/36.9; 428/36.91; 604/96.01; 604/103.05; 604/103.06; 604/103.08; 604/103.11; 604/103.13; 604/264; 604/523
(58) Field of Search ............. 604/93.01, 96.01, 604/101.01, 101.02, 103, 103.05, 103.06, 103.08, 103.11, 103.13, 264, 523; 428/34.1, 35.2, 35.7, 36.5, 36.8, 36.9, 36.91

(56) References Cited

U.S. PATENT DOCUMENTS

| | | | | |
|---|---|---|---|---|
| 4,154,244 A | * | 5/1979 | Becker et al. | ......... 604/103.11 |
| 4,431,813 A | * | 2/1984 | Handte et al. | ............... 548/165 |
| 5,195,970 A | | 3/1993 | Gahara | |
| 5,328,468 A | * | 7/1994 | Kaneko et al. | ................ 604/96 |
| 5,374,473 A | | 12/1994 | Knox et al. | |
| 5,451,439 A | * | 9/1995 | Bigg | ......................... 428/36.8 |

(Continued)

FOREIGN PATENT DOCUMENTS

| | | |
|---|---|---|
| GB | 2 008 140 A | 5/1979 |
| WO | WO 95/05555 | 2/1995 |
| WO | WO 98/32474 | 7/1998 |
| WO | WO 99/26691 | 6/1999 |
| WO | WO 02/081018 A1 | 10/2002 |

OTHER PUBLICATIONS

Hawley's Condensed Chemical Dictionary, 1997, John Wiley & Sons, Inc., Thirteenth Edition, pp. 437 and 1175.*

"Standard Test Methods for Vulcanized Rubber and Thermoplastic Elastomers—Tension", ASTM, Designation: D412–98a, pp. 1–13.

Daniels, C.A., *POLYMERS: Structure and Properties*, Technomic Publishing Co., Inc., 1989, pp. 94–95.

Dictionary entry for "elastomer," McGraw–Hill Encyclopedia of Science & Technology Online, Jan. 10, 2005.

Primary Examiner—Harold Pyon
Assistant Examiner—Walter B Aughenbaugh
(74) Attorney, Agent, or Firm—Fulwider Patton Lee & Utecht, LLP (57) ABSTRACT

A catheter balloon formed of a polymeric material such as expanded polytetrafluoroethylene (ePTFE) bonded to a second layer formed of a low tensile set polymer and/or impregnated with a low tensile set polymer. In a presently preferred embodiment, the low tensile set polymer is a silicone-polyurethane copolymer elastomer or a diene polymer elastomer. The low tensile set polymer has high strength, low modulus, high elongation, and low tensile set. The diene or silicone-polyurethane has a low tensile set, which facilitates deflation of the balloon to a low profile deflated configuration. One aspect of the invention provides improved attachment of the diene to the ePTFE. In one embodiment, the second layer is formed of a diene mixed with a bonding promoter such as a vulcanizing agent which is covalently bonded to the diene.

17 Claims, 2 Drawing Sheets

U.S. PATENT DOCUMENTS

| | | | |
|---|---|---|---|
| 5,752,934 A | * | 5/1998 | Campbell et al. ............. 604/96 |
| 5,804,263 A | * | 9/1998 | Goldberg et al. .......... 428/34.7 |
| 5,807,327 A | | 9/1998 | Green et al. |
| 5,868,704 A | * | 2/1999 | Campbell et al. ............. 604/96 |
| 6,016,848 A | | 1/2000 | Egres, Jr. |
| 6,099,563 A | * | 8/2000 | Zhong ....................... 623/1.46 |
| 6,120,477 A | * | 9/2000 | Campbell et al. ............. 604/96 |
| 6,132,824 A | | 10/2000 | Hamlin |
| 6,139,517 A | * | 10/2000 | Macoviak et al. ............. 604/8 |
| 6,139,525 A | * | 10/2000 | Davis-Lemessy et al. .. 604/103 |
| 6,195,805 B1 | * | 3/2001 | Bourne et al. ................. 2/168 |
| 6,238,408 B1 | * | 5/2001 | Kawabata et al. .......... 606/192 |
| 6,284,856 B1 | * | 9/2001 | Lee ......................... 526/329.2 |
| 6,344,045 B1 | * | 2/2002 | Lim et al. ................... 606/108 |
| 6,391,409 B1 | * | 5/2002 | Yeh et al. .................. 428/35.7 |
| 6,533,806 B1 | | 3/2003 | Sullivan et al. |
| 6,544,217 B1 | * | 4/2003 | Gulachenski ............ 604/96.01 |
| 6,547,760 B1 | * | 4/2003 | Samson et al. ........ 604/103.01 |
| 6,602,224 B1 | | 8/2003 | Simhambhatla |
| 6,695,809 B1 | * | 2/2004 | Lee ......................... 604/96.01 |
| 2001/0014717 A1 | * | 8/2001 | Hossainy et al. |
| 2002/0010420 A1 | | 1/2002 | Bagaoisan et al. |
| 2002/0146557 A1 | | 10/2002 | Claude et al. |
| 2002/0187288 A1 | | 12/2002 | Lim et al. |
| 2003/0018156 A1 | * | 1/2003 | Meijs et al. |

* cited by examiner

CATHETER BALLOON FORMED OF EPTFE AND A DIENE POLYMER

BACKGROUND OF THE INVENTION

This invention generally relates to medical devices, and particularly intracorporeal devices for therapeutic or diagnostic uses, such as balloon catheters. In percutaneous transluminal coronary angioplasty (PTCA) procedures, a guiding catheter is advanced until the distal tip of the guiding catheter is seated in the ostium of a desired coronary artery. A guidewire, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g., greater than 8 atmospheres) so that the stenosis is compressed against the arterial wall to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as DACRON, may be implanted in vessels to strengthen or repair the vessel, or used in an anastomosis procedure to connect vessels segments together.

In the manufacture of catheters, one difficulty has been the bonding of dissimilar materials together. The fusion bonding of a dissimilar material to a substrate material can be extremely difficult if the substrate has a low surface energy. For example, lubricious materials such as HDPE and PTFE, often used to form inner tubular members of catheters to provide good guidewire movement therein, have low surface energies of 31 dynes/cm and 18 dynes/cm, respectively, that make bonding to balloons formed of a dissimilar material such as a polyamide difficult. Prior attempts to address this problem involved providing a multilayered shaft having an outer layer on the shaft configured to be bondable to the balloon. However, a decrease in shaft collapse pressure resistance may result in some cases when the outer layer has a low stiffness. While adhesives may be used in some cases to bond dissimilar materials together, they are not ideal because they can increase stiffness of the component at the bond and some materials do not bond well to adhesives commonly used in medical devices.

A catheter balloon formed of expanded polytetrafluoroethylene (ePTFE) has been suggested. ePTFE is PTFE which has been expanded to form porous ePTFE which typically has a node and fibril microstructure comprising nodes interconnected by fibrils. However, ePTFE has proven difficult to bond to balloon liner materials and/or to catheter shafts. One difficulty has been bonding ePTFE absent the use of adhesives and/or some pretreatment causing decomposition of the fibril structure.

It would be a significant advance to provide a catheter balloon, or other medical device component, with improved performance and bondability.

SUMMARY OF THE INVENTION

This invention is directed to a catheter balloon formed of a polymeric material such as expanded polytetrafluoroethylene (ePTFE) bonded to a second layer formed of a low tensile set polymer and/or impregnated with a low tensile set polymer. In a presently preferred embodiment, the low tensile set polymer is an elastomer selected from the group consisting of a silicone-polyurethane copolymer and a diene polymer. The low tensile set polymer has high strength, low modulus, high elongation, and low tensile set, to provide improved balloon performance. Specifically, the silicone-polyurethane or diene has a low tensile set which facilitates deflation of the balloon to a low profile deflated configuration. In a presently preferred embodiment, the balloon has a low radial tensile set of about 1% to about 20%, preferably about 1% to about 10%.

In one embodiment, the low tensile set polymer is a silicone-polyurethane copolymer. A presently preferred silicone-polyurethane is an ether urethane and more specifically an aliphatic ether urethane such as PURSIL AL 575A and PURSIL AL10, available from Polymer Technology Group, and ELAST-EON 3-70A, available from Elastomedics, which are silicone polyether urethane copolymers, and more specifically, aliphatic ether urethane cosiloxanes. The presently preferred silicone-polyurethane copolymers have a high elongation of greater than about 400%, a sufficiently low initial modulus of about 300 psi to about 2100 psi to minimally affect the compliance of the ePTFE layer, and a high tensile strength of about 3000 psi to about 6500 psi to retract the ePTFE layer after radial expansion of the balloon.

The presently preferred silicone-polyurethane copolymers have a low inelastic stress response or tensile set (i.e., the extension remaining after a specimen has been stretched and allowed to retract in a specified manner, expressed as a percentage of original size; see ASTM D412). In a balloon having a first layer (e.g., an ePTFE layer), and a second layer formed of a silicone-polyurethane copolymer, the silicone-polyurethane layer has a low radial tensile set of about 0% to about 10%, preferably about 1% to about 5%, after radial expansion to about 300% or more of the initial radial dimension, providing a balloon having a low radial tensile set of about 1% to about 20%, preferably about 1% to about 10%. Consequently, the balloon retracts to a low profile deflated configuration, despite the inelasticity of the ePTFE layer. Similarly, the silicone-polyurethane layer has a low axial tensile set of about 0% to about 10%, preferably about 1% to about 5%, after axial expansion to about 300% or more of the initial axial dimension. In radial tensile set measurements, the initial diameter of a polymer tube is measured and the tube is expanded radially to 300% or more of the initial diameter, the strain is maintained for one minute and then removed to allow the tube to retract, and the diameter of the retracted tube is measured after one minute. Axial tensile set measurements are similarly made on a polymer tube stretched longitudinally to 300% or more of the initial length.

In another embodiment, the low tensile set polymer is a diene polymer. A variety of suitable diene polymers can be used in a balloon embodying features of the invention, including an isoprene such as an AB and ABA poly(styrene-block-isoprene), a neoprene, an AB and ABA poly(styrene-block-butadiene) such as styrene butadiene styrene (SBS) and styrene butadiene rubber (SBR), and 1,4-polybutadiene. In a presently preferred embodiment, the diene polymer is an isoprene including isoprene copolymers and isoprene block copolymers such as poly(styrene-block-isoprene). A presently preferred isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1, 3-butadiene) available from Dupont Elastomers. Neoprene grades useful in the invention include HT 501 available from Apex Medical, and neoprene (i.e., polychloroprene) available from Dupont Elastomers, including Neoprene G, W, T and A types available from Dupont Elastomers. The presently preferred diene polymers have a high elongation of greater than about 300%, a low modulus of about 50 psi to about 3500 psi to minimally affect the compliance of the ePTFE layer, and a high strength of about 3000 psi to about 10,000 psi to retract the ePTFE layer after radial expansion of the balloon.

In a balloon having a first layer (e.g., an ePTFE layer), and a second layer formed of a diene polymer, the diene layer has a low radial tensile set of about 0% to about 25%, preferably about 0% to about 10%, most preferably about 1% to about 5%, after radial expansion to about 300% or more of the initial radial dimension, providing a balloon having a low radial tensile set of preferably about 1% to about 20%, most preferably about 1% to about 10%. In the embodiment in which the diene layer is formed of an isoprene, the diene layer has a very low radial and axial tensile set of about 0% to about 10%, preferably about 1% to about 5%, and more specifically about 2% to about 5%, after expansion to 300% or more of the initial dimension. In one embodiment, a diene layer formed of a neoprene has a radial tensile set of about 16% to about 18%.

The low tensile set polymer layer is bonded to the ePTFE layer preferably by fusion bonding, although adhesive bonding may alternatively be used. In one embodiment, the ePTFE layer is coated or impregnated with a bondable material to improve the bonding of the ePTFE layer to the low tensile set polymer layer. In one embodiment, the bondable material on the ePTFE first layer is a plasma polymerized functionality bonded to at least a section of the ePTFE layer, Alternatively, the bondable material is a polymer impregnated in the ePTFE.

Suitable plasma polymerized films for use as the bondable material on the ePTFE, including desirable monomers, RF field strengths, and co-reactants, are disclosed in U.S. patent application Ser. No. 09/827,887, incorporated in its entirety by reference herein. In plasma polymerization, free-radical organic species, such as fragmented acrylic acid, in the plasma will couple with the surface of the ePTFE substrate, resulting in a crosslinked thin film which is covalently bonded to the ePTFE. It forms a permanent surface modification, unlike plasma etching processes in which any beneficial effects on the surface energy of the substrate quickly decrease as a function of time as described by Yasuda and Sharma, J. Polym. Sci. Polym. Phys., Ed. 19:1285 (1981), incorporated in its entirety by reference herein. The plasma polymerized film covalently bonded to the ePTFE enhances adhesion of the ePTFE to the second layer, for example via hydrogen bonding, or to an adhesive bondable to the second layer. It thus allows for bonding the ePTFE layer to a second layer formed of a low tensile set polymer which is incompatible with or otherwise not readily bondable to ePTFE. The plasma polymerized film has manufacturing advantages minimal effect on the compliance of the ePTFE layer. The plasma polymerized film may comprise a variety of suitable functionality including carboxylate, amine, and sulfonate groups, which are polymerized on at least a surface of the substrate of the medical device component. In a presently preferred embodiment, the plasma polymerized carboxylate film comprises an acrylate or acrylate-like polymer layer deposited onto the ePTFE by exposing the ePTFE film to a plasma, which in a presently preferred embodiment is an acrylic acid plasma. One of skill in the art will recognize that some fragmentation of the acrylate typically occurs as the result of plasma polymerization, producing an acrylate-like polymer layer of fragmented acrylate. In a presently preferred embodiment, the surface is carboxylate-rich from an acrylic acid plasma. However, a variety of suitable plasma polymerized films may be used as the bondable material on the ePTFE layer, including plasma polymerized allyl amine providing an amine-rich film. The plasma polymerized film is typically crosslinked to varying degrees depending on the nature of the reactive species in the plasma which form the film and the radiofrequency (RF) intensity used in the plasma polymerization process.

Dienes are typically incompatible with or otherwise not readily fusion bondable to ePTFE, and one aspect of the invention provides for improved attachment of the diene to the ePTFE. In one embodiment, the balloon has a first layer formed of ePTFE coated or impregnated with a bondable material, and a second layer formed of the mixture of the diene polymer and a bonding promoter. The bonding promoter covalently bonds to unsaturation of the diene, and bonds to the bondable material on or in the ePTFE layer. In one embodiment, the bonding promoter facilitates bonding the balloon to the catheter shaft. For example, shaft materials including polyamides and polyurethanes which are not readily fusion bondable to dienes are fusion bondable to the diene-bonding promoter second layer of a balloon embodying features of the invention. The covalent bonding of the bonding promoter to the diene of the second layer can occur before of during fusion bonding of the balloon to the catheter shaft.

In one embodiment, the bonding promoter is an amphiphilic material, preferably selected from the group consisting of a thiol with a functionality such as an amine or carboxylic acid functionality, a thiuram, a mercapto amine, a mercapto epoxide, dansyl chloride, and thionin acetate. The bonding promoter may have a variety of suitable polar functionalities such as pendant amine groups which bond to acid-rich bondable materials on the modified ePTFE layer, or carboxylic acid groups or epoxide groups which bond to amine-rich bondable materials on the modified ePTFE layer. In one presently preferred embodiment, the bonding promoter is a vulcanizing agent. In one embodiment, the vulcanizing agent is selected from the group consisting of a thiol with a functionality such as an amine or carboxylic acid functionality, a mercapto epoxide, a mecapto amine, and a thiuram. More specifically, in one embodiment, the bonding promoter is selected from the group consisting of a mercaptobenzothiazole such as 6-amino, 2-mercaptobenzothiazole, and a thiuram disulfide compound such as tetraamino alkyl thiuram disulfide. The vulcanizing agent (i.e., bonding promoter) vulcanizes the diene and hydrogen-bonds to the bondable material on the ePTFE layer. Specifically, the vulcanizing agent has a vulcanizing functionality such as a mercapto group which covalently bonds to the diene, and a polar functionality such as amine groups which bond, as for example by hydrogen-bonding, to the bondable material of the ePTFE. Thus, when the diene-vulcanizing agent mixture is heated to cause vulcanization, the vulcanizing agent covalently bonds to the diene, and provides a polar functionality which allows for adhesion or fusion bonding of the vulcanized diene second layer to the modified ePTFE first layer. The vulcanizing agent bonds to the diene without necessarily cross-linking the diene.

The bonding promoter in the diene second layer bonds to the bondable material on the ePTFE first layer, such bondable materials including a plasma polymerized functionality bonded to at least a section of the ePTFE layer or a polymer such as a diene polymer impregnated in the ePTFE. In one embodiment, the diene polymer to be impregnated in the ePTFE is mixed with a bonding promoter which preferably is a vulcanizing agent which vulcanizes the impregnated diene. The vulcanized diene (i.e., the bondable material) impregnated in the ePTFE first layer hydrogen-bonds to a polar functionality of the bonding promoter in the diene second layer, thereby bonding the ePTFE first layer to the diene second layer of the balloon.

In another embodiment, the balloon has at least a first layer formed of a porous material such as ePTFE impregnated with a low tensile set polymer such as a silicone-polyurethane copolymer or a diene polymer. In one embodiment, the ePTFE is impregnated with a solution of the silicone-polyurethane copolymer or diene polymer, so that the polymer impregnates the pores of the ePTFE. Typically, an inner surface of the ePTFE tube is exposed to the silicone-polyurethane copolymer or diene polymer solution in the inner lumen of the ePTFE tube to impregnate the ePTFE tube, and the polymer also coats the inner surface of the ePTFE tube. In one embodiment, the diene polymer to be impregnated in the ePTFE is mixed with the bonding promoter discussed above which covalently bonds to unsaturation of the diene polymer impregnated in the ePTFE, as for example by vulcanizing the diene polymer impregnated in the ePTFE. The balloon formed of the impregnated ePTFE layer may optionally include a second layer formed of a second polymer bonded to the impregnated ePTFE layer. The second layer may be adhesively or fusion bonded to the impregnated ePTFE layer, and is preferably fusion bonded. In one embodiment, the second polymer forming the second layer is a diene, which in one embodiment is mixed with the bonding promoter discussed above which covalently bonds to unsaturation of the diene polymer of the second layer, as for example by vulcanizing the diene polymer of the second layer, and hydrogen-bonds to the bonding promoter-diene mixture impregnated in the ePTFE, so that the layers are fusion, e.g., heat fusion, bondable together.

In another embodiment, the balloon has a first layer formed of a polymeric material such as ePTFE adhesively bonded to a second layer formed of a low tensile set polymer. The low tensile set polymer is preferably a silicone-polyurethane copolymer, or a diene polymer preferably selected from the group consisting of an isoprene and a neoprene.

In one embodiment of a method of making a balloon for a catheter, which embodies features of the invention, a first layer formed of a polymeric material such as ePTFE coated or impregnated with a bondable material is positioned against a second layer and the layers heated to fusion bond together. In one embodiment, the second layer is formed of a mixture of a diene polymer and a bonding promoter which covalently bonds to the diene polymer and bonds to the bondable material of the ePTFE first layer. With the first layer positioned against the second layer, the layers are heated to fusion bond the layers together, and the diene layer may be heated to couple the diene to the bonding promoter prior to being positioned against the first layer, or alternatively, the two layers are positioned together and heated to both couple the diene to the bonding promoter in the second layer and to fusion bond the diene second layer to the ePTFE first layer.

In an alternative method of making a balloon for a catheter, which embodies features of the invention, a first layer of formed of a polymeric material such as ePTFE is exposed to an aqueous or organic solution of a low tensile set polymer, so that the polymer impregnates the ePTFE by completely or partially filling the pores of the ePTFE.

The balloon of the invention can be used with a variety of suitable balloon catheters including coronary angioplasty catheters, peripheral dilatation catheters, stent delivery catheters, drug delivery catheters, and the like. Balloon catheters of the invention catheter generally comprise an elongated shaft with at least one lumen and balloon on a distal shaft section with an interior in fluid communication with the at least one lumen. The ePTFE tubular layer can be formed using conventional methods, generally including wrapping a sheet of ePTFE around a mandrel and heat fusing the wrapped material together to form a tube. The ePTFE generally is porous, and typically has a node and fibril microstructure. Although discussed primarily in terms of a balloon formed of ePTFE, it should be understood that the balloon may comprise other substrates including polymers having a porous structure, polyethylene and fluoropolymers in general, and polymers having a node and fibril microstructure including ultrahigh molecular weight polyolefin such as ultrahigh molecular weight polyethylene, and polypropylene, where conventional fusion bonding fails and surface modification is required. It should be understood that a balloon having a layer formed of a porous material such as ePTFE or ultra high molecular weight polyethylene may have the pores of the porous material partially or completely filled by another polymeric material.

The balloon of the invention has improved performance characteristics such as a low profile deflated configuration, high strength, flexibility and conformability, and improved manufacturability. Additionally, the balloon has excellent adhesion between the ePTFE (or other polymer) and the silicone-polyurethane copolymer or diene polymer, with minimal effect on the structural integrity of the ePTFE material, unlike chemical modification involving decomposition of the ePTFE. These and other advantages of the invention will become more apparent from the following detailed description when taken in conjunction with the accompanying exemplary drawings.

DETAILED DESCRIPTION OF THE INVENTION

Figure 1:
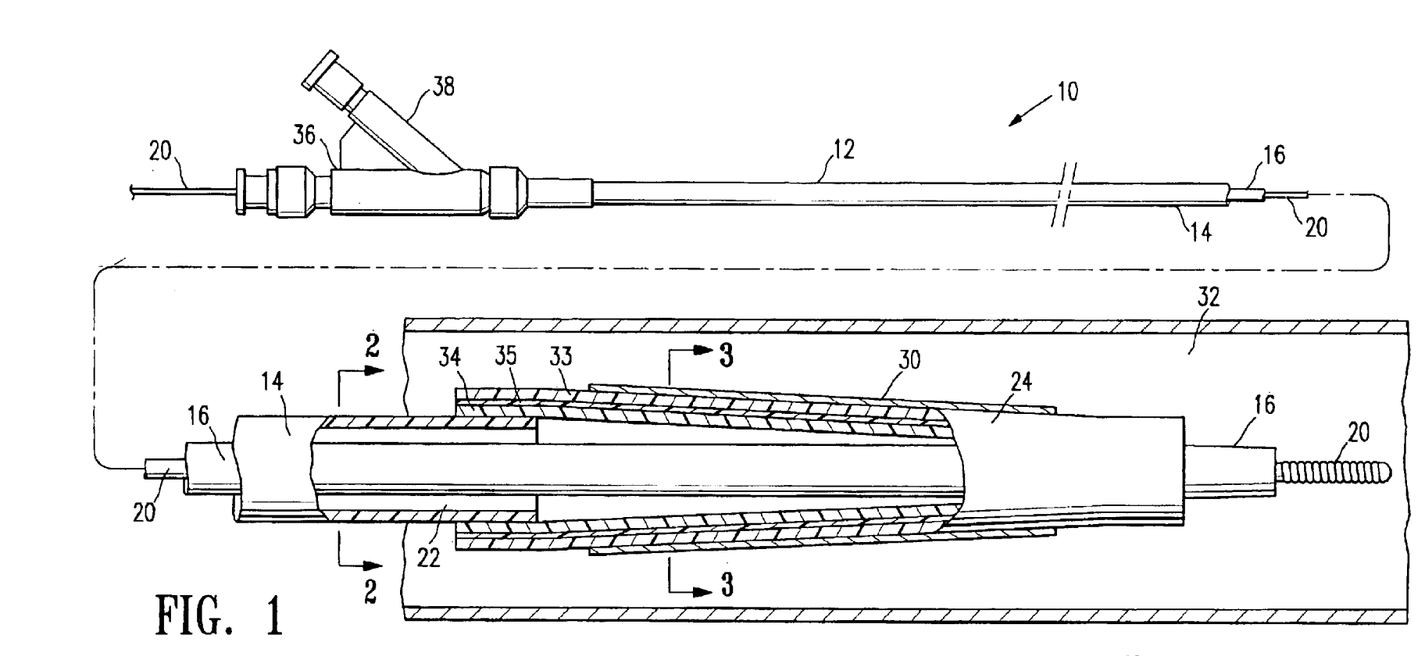
FIG. 1 is an elevational view, partially in section, of a balloon catheter for delivering a stent, that embodies features of the invention, having a balloon with a first layer formed of ePTFE and a second layer formed of a low tensile set polymer bonded to the first layer.
Figure 2:
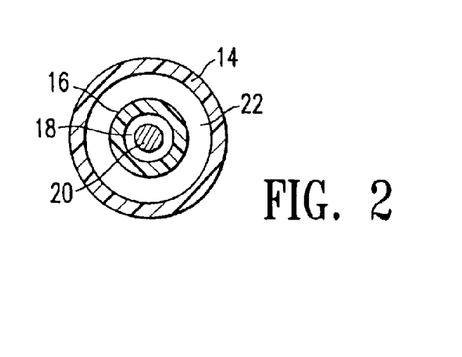
FIG. 2 is a transverse cross-section of the catheter shown in FIG. 1 taken at line 2—2.
Figure 3:
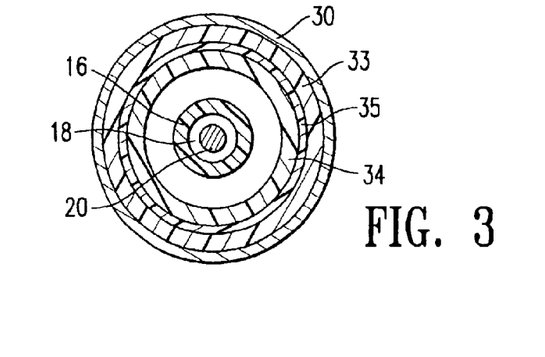
FIG. 3 is a transverse cross-section of the catheter shown in FIG. 1 taken at line 3—3.

FIGS. 1–3 illustrate an over-the-wire type stent delivery balloon catheter 10 embodying features of the invention. Catheter 10 generally comprises an elongated catheter shaft 12 having an outer tubular member 14 and an inner tubular member 16. As best illustrated in FIGS. 2 and 3, showing transverse cross sections of the catheter of FIG. 1, taken along lines 2—2 and 3—3, respectively, inner tubular member 16 defines a guidewire lumen 18 configured to slidingly receive a guidewire 20, and the coaxial relationship between outer tubular member 14 and inner tubular member 16 defines annular inflation lumen 22. An inflatable balloon 24 disposed on a distal section of catheter shaft 12 has a proximal skirt sealingly secured to the distal end of outer tubular member 14 and a distal skirt sealingly secured to the distal end of inner tubular member 16, so that its interior is in fluid communication with inflation lumen 22. An adapter 36 at the proximal end of catheter shaft 12 is configured to direct inflation fluid through arm 38 into inflation lumen 22 and to provide access to guidewire lumen 18. Balloon 24 has an inflatable working length located between tapered sections of the balloon. An expandable stent 30 is mounted on balloon working length. FIG. 1 illustrates the balloon 24 in an uninflated configuration prior to deployment of the stent 30. The distal end of catheter may be advanced to a desired region of a patient's body lumen 32 in a conventional manner, and balloon 24 inflated to expand stent 30, seating the stent in the body lumen 32.

In the embodiment illustrated in FIG. 1, the balloon 24 comprises a first layer 33 formed of a porous material, preferably having a node and fibril microstructure, such as ePTFE, and a second layer 34 formed of a low tensile set polymer such as a silicone-polyurethane copolymer or a diene polymer. In a preferred embodiment, layer 34 is an inner layer relative to layer 34, although in other embodiments it may be an outer layer relative to layer 33. Layer 34 limits or prevents leakage of inflation fluid through the microporous ePTFE to allow for inflation of the balloon 24, and is highly elastic to facilitate deflation of the balloon 24 to a low profile deflated configuration. In the embodiment of FIG. 1, the layer 34 is a separate layer which neither fills the pores nor disturbs the node and fibril structure of the ePTFE layer. In an alternative embodiment, a polymer such as a diene polymer at least partially fill the pores of an ePTFE layer. Typically, the ePTFE comprises a film of stretched material which is formed into the tubular member layer 33 by wrapping the ePTFE material around a mandrel to form a tube and then heating the wrapped material to fuse the wrapped material together.

In the embodiment illustrated in FIG. 1, the ePTFE layer 33 of the balloon 24 is chemically modified to provide a plasma polymerized film 35 which facilitates bonding layer 33 to layer 34. At least a section of the ePTFE layer 33, and preferably the entire length of at least an inner surface of ePTFE layer 33, has the plasma polymerized film 35. However, in alternative embodiments, less than the entire length may be chemically modified, by masking a part of the ePTFE substrate using methods conventionally known in the field. The thickness of the plasma polymerized film 35, which is exaggerated in FIG. 1 for ease of illustration, is about 10 nm to about 150 nm thick, preferably about 10 nm to about 50 nm thick. In a presently preferred embodiment, the balloon is chemically modified to create a carboxylate-rich surface. However, a variety of suitable functionalities can be plasma polymerized on the surface of the balloon including amine, and sulfate functionalities. In a presently preferred embodiment, the plasma polymerized carboxylate film comprises an acrylate or acrylate-like polymer layer deposited onto the ePTFE by exposing the ePTFE film to a plasma, which in a presently preferred embodiment is an acrylic acid plasma. While discussed below primarily in terms of applying a carboxylate film by plasma polymerization of acrylic acid on ePTFE, it should be understood that a variety of functionalities may be used.

In the embodiment in which the second layer 34 is formed of a silicone-polyurethane copolymer, the second layer 34 is readily fusion bondable to plasma polymerized acrylic acid treated ePTFE layer 33 having a plasma polymerized carboxylate film thereon. Additionally, second layer 34 formed of a silicone-polyurethane copolymer is fusion bondable to conventional polymeric materials such as polyamides and polyurethanes which may be used to form catheter shaft 12. The silicone-polyurethane is typically melt extruded into a tubular shape to form layer 34, although the silicone-polyurethane layer 34 may alternatively be formed by processes such as dip coating. A variety of suitable silicone-polyurethane copolymers may be used for layer 34, including an aliphatic ether urethane cosiloxane, which in one embodiment has about 1% to about 20% cosiloxane. In one embodiment, the silicone-polyurethane copolymer layer 34 has a low radial tensile set of less than about 10%. After five inflations to nominal diameter, tubing formed of PURSIL-AL 575A having an initial outer diameter of about 0.045 inches had a radial tensile set and an axial tesile set of less than 10%.

In one embodiment, the second layer 34 is formed of a diene polymer selected from the group consisting of an isoprene, a neoprene, 1,4-polybutadiene, a poly(styrene-block-isoprene), and a poly(styrene-block-butadiene). In one embodiment, the diene layer 34 has a low radial tensile set of less than about 20%, preferably less than about 10%. In a presently preferred embodiment, the diene polymer forming second layer 34 is an isoprene, including a poly(styrene-block-isoprene). Isoprenes are not readily bondable to ePTFE absent an additional agent which facilitates bonding to the ePTFE layer 33.

Preferably, the diene second layer 34 includes a bonding promoter (not shown) mixed with the diene, which covalently bonds to the diene and bonds to the surface modified ePTFE of layer 33. In a presently preferred embodiment, the bonding promoter vulcanizes the diene and hydrogen-bonds to the plasma polymerized functionality 35 on the ePTFE layer 33, allowing layer 33 to heat fusion bond to layer 34. For example, the amine polar functionality of a bonding promoter selected from the group consisting of 6-amino, 2-mercaptobenzothiazole and tetraamino alkyl thiuram disulfide allows for heat fusion bonding to an acid-rich plasma polymerized film 35 on the ePTFE layer 33, such as an acrylic acid rich surface of a plasma polymerized acrylate film. Thus, the plasma polymerized functionality is a bondable material on an inner surface of the ePTFE layer, which hydrogen-bonds to the polar functionality of the vulcanized bonding promoter forming the diene second layer 34, allowing the layers 33 and 34 to heat fusion bond together. While discussed below in terms of a bonding promoter which vulcanizes the diene, it should be understood that a variety of suitable bonding promoters may be used which covalently bond to unsaturation of the diene.

The mixture of the diene polymer and bonding promoter typically has about 0.5% to about 3% by weight of the bonding promoter. In a presently preferred embodiment, the amount of bonding promoter is insufficient to react with all the unsaturation of the diene, so that the second layer 34 is a diene having at least some unsaturation remaining following the reaction with the bonding promoter. Depending on the method used to form the diene layer 34, the diene polymer and bonding promoter are typically mixed together in the form of a solution, or alternatively, mixed and melted as solids. For example, in one embodiment, a solution of the bonding promoter in a solvent such as tetrahydrofuran (THF) is blended into a solution of the diene polymer in a solvent such as THF. The resulting solution is applied to a mandrel, for example by dip coating, and dried to form a film which, after removing from the mandrel, forms tubular diene layer 34. Alternatively, solid pellets of the diene polymer and bonding promoter are mixed and melted together, and melt extruded using conventional extrusion methods to form tubular diene layer 34. With the thus formed tubular diene layer 34 on a mandrel and typically already bonded to the inner and outer tubular members of the shaft, the tubular ePTFE layer 33 having a plasma polymerized functionality bonded thereto is placed around the diene layer 34. A Teflon sheath is positioned over the ePTFE layer 33, and the layers 33 and 34 are exposed to elevated temperature and pressure to laminate the layers 33 and 34 together, preferably using balloon press equipment. The balloon press apparatus uniformly heats the ePTFE and diene liner layers 33 and 34. For example, in one embodiment, the layers 33 and 34 are heated at about 100° C. to about 150° C. and a radially compressing pressure of about 10 psi to about 50 psi is applied for about 10 to about 120 seconds, which fusion bonds the layers 33 and 34 together, thereby forming balloon 24. In one embodiment, the diene layer 34 has not been heated to bond the diene to the bonding promoter mixed therewith (e.g., vulcanize the diene layer) prior to being positioned against the ePTFE layer 33, so that heating the two layers both vulcanizes the diene layer and fusion bonds the vulcanized diene layer to the ePTFE layer 33.

In an alternative embodiment (not shown), a balloon having ePTFE first layer 33 and second layer 34 (e.g., diene or silicone-polyurethane second layer 34) includes an adhesive between ePTFE layer 33 and layer 34 to adhesively bond layers 33 and 34 together. A variety of suitable adhesives commonly used in the medical device field may be used. In one embodiment, the adhesive bonds layer 33 to layer 34 without the use of plasma polymerized film 35 on layer 33 or a bonding promoter mixed with the diene of layer 34. However, in one embodiment, a plasma polymerized film 35 is provided on layer 33 to facilitate bonding the adhesive to layer 33. In the embodiment illustrated in FIG. 1, balloon 24 is secured to the shaft 12 by heat fusion or adhesively bonding layer 34 to the outer surface of the outer tubular member 14 and inner tubular member 16. In the embodiment in which the diene layer 34 includes the bonding promoter, the layer 34 is preferably heat fusion bonded to the outer surface of the shaft outer tubular member 14 and inner tubular member 16, to secure the balloon 24 to the shaft. The bonding promoter thus facilitates heat fusion bonding the diene layer 34 to conventional catheter shaft materials such as polyurethanes and polyamides, which otherwise would not readily bond to the diene polymer. Using conventional heat/laser bonding methods, the balloon proximal skirt is placed over the distal section of the outer tubular member 14, and the balloon distal skirt is placed over the distal section of the inner tubular member 16, and heat applied to the balloon skirt sections to melt or soften the polymeric material. A heat shrink sleeve may also be used during heat fusion bonding which shrinks to provide pressure at the bond site. In an alternative embodiment (not shown), the layer 34 does not extend the entire length of the ePTFE layer 33, so that one or both end sections of the chemically modified ePTFE layer 33 having plasma polymerized functionality 35 thereon are heat fusion or adhesively bonded directly to the shaft. Although discussed primarily in terms of fusion bonding the balloon 24 to the shaft 12, in an alternative embodiment, the two components are adhesively bonded together. A variety of suitable adhesives commonly used in the medical device field may be used, and preferably adhesives such as acrylates, epoxies, and urethanes, and the adhesive is applied as is conventionally known by spraying, dipping or otherwise coating a section of the shaft to be bonded.

Figures 4, 5, 7:
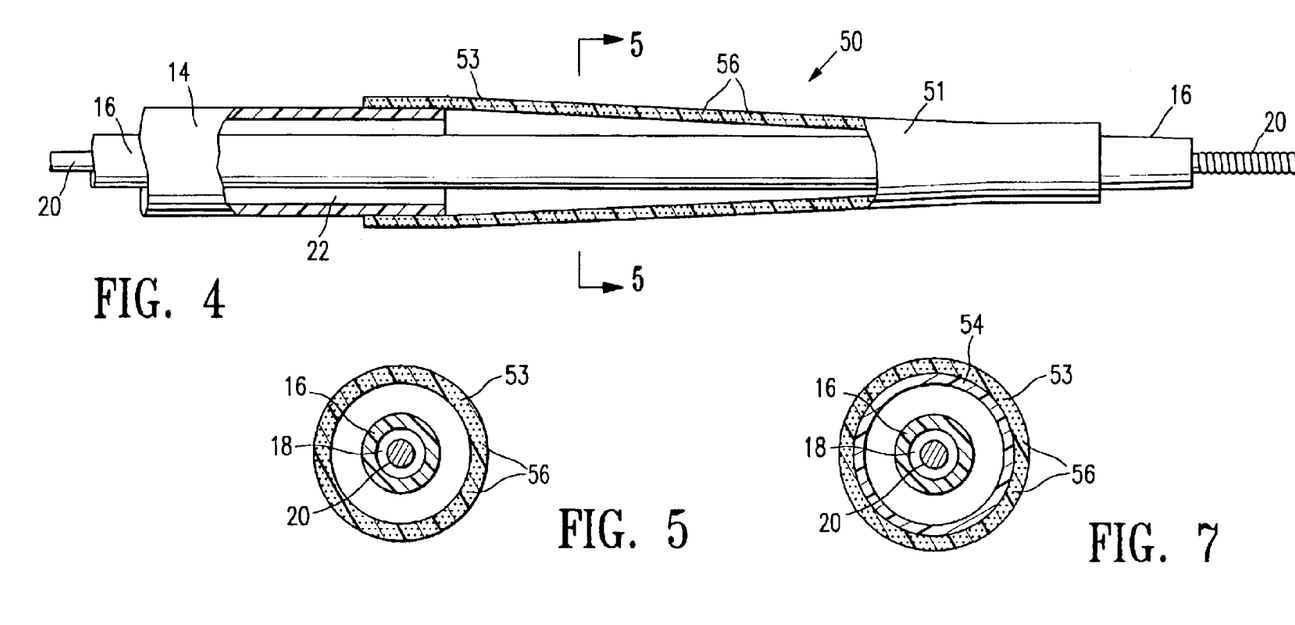
FIG. 4 is a longitudinal cross section of a distal end of an alternative embodiment of a balloon catheter that embodies features of the invention, having a balloon with a single layer impregnated with a polymer.
FIG. 5 is a transverse cross-section of the catheter shown in FIG. 4 taken at line 5—5.
FIG. 7 is a transverse cross-section of the catheter shown in FIG. 6 taken at line 7—7.

FIG. 4 illustrates the distal end of an alternative balloon catheter 50 which embodies features of the invention, similar to balloon catheter 10 of FIG. 1, but having a balloon 51 bonded to outer tubular member 14 and inner tubular member 14. FIG. 5 illustrates a transverse cross section of the balloon catheter of FIG. 4, taken along line 5—5. Balloon 51 comprises at least a first layer 53 formed of ePTFE impregnated with a low tensile set polymer 56 such as a silicone-polyurethane copolymer or a diene polymer. For example, a diene solution is formed by dissolving a diene in an organic solvent such as THF, or by dissolving a water-based diene in water, to form a diene solution having a concentration of about 5% to about 25%, and preferably about 5% to about 15%. The solution is coated onto the inside of an ePTFE tube using a variety of suitable methods. In one embodiment, diene solution is injected into the lumen of the ePTFE tube using a syringe or other device to deliver the diene solution, preferably after one end of the ePTFE tube is reversibly closed for example by being tied or otherwise blocked. Excess solution is removed from the ePTFE tube lumen, leaving diene solution in the porous structure of the ePTFE and on the inner surface of the ePTFE tube. In an alternative embodiment, the ePTFE tube is inserted inside a container, such as a glass mold, with the diene polymer solution in the container, and a vacuum is applied to the lumen of the ePTFE tube to draw the diene polymer solution up into the ePTFE tube lumen. The vacuum is turned off and the diene polymer solution allowed to drain off from inside the ePTFE tube leaving the diene solution as in the above method. The diene polymer solution may include surfactants, such as fluorocarbon surfactants including FC 430 and FC 129 available from 3M, or Zonyl available from Zeneca, to form a compatible interface between the ePTFE node and fibril structure and the diene polymer. Additionally, the inner surface of the ePTFE tube can be plasma etched, using for example an argon plasma, to improve surface wetability. The thus coated ePTFE tube is exposed to elevated temperature or blown air (elevated or ambient temperature), to evaporate the solvent. The resulting ePTFE tube has diene polymer 56 impregnated in the pores of the ePTFE and thus mechanically connected to the ePTFE tube. Although not illustrated, some of the diene polymer 56 typically coats an inner surface of the ePTFE tube, so that it is preferably at least in part on an inner surface of the ePTFE layer 53. The resulting impregnated ePTFE layer 53 is completely or partially impregnated with the diene polymer 56, and in a presently preferred embodiment is partially impregnated with the diene polymer. Although discussed in terms of a diene polymer 56, ePTFE layer 53 can be similarly impregnated with a silicone-polyurethane copolymer.

In one embodiment, the diene polymer impregnated in the ePTFE layer 53 includes a bonding promoter mixed therewith. The discussion above relating to the bonding promoter mixed with the diene layer 34 of the embodiment of FIG. 1 applies to the bonding promoter mixed with the diene polymer impregnated in the ePTFE layer 53 of the embodiment of FIG. 4. Thus, the bonding promoter preferably covalently bonds to unsaturation of the diene polymer impregnated in the ePTFE layer 53, for example by vulcanizing the diene polymer impregnated in the ePTFE layer 53. In one embodiment, the diene-bonding promoter mixture impregnated in the ePTFE promotes hydrogen bonding of the impregnated ePTFE layer 53 to the catheter shaft. The covalent bonding (e.g., vulcanization) between the diene and the bonding promoter can occur before or during bonding of the balloon to the shaft.

Figure 6:
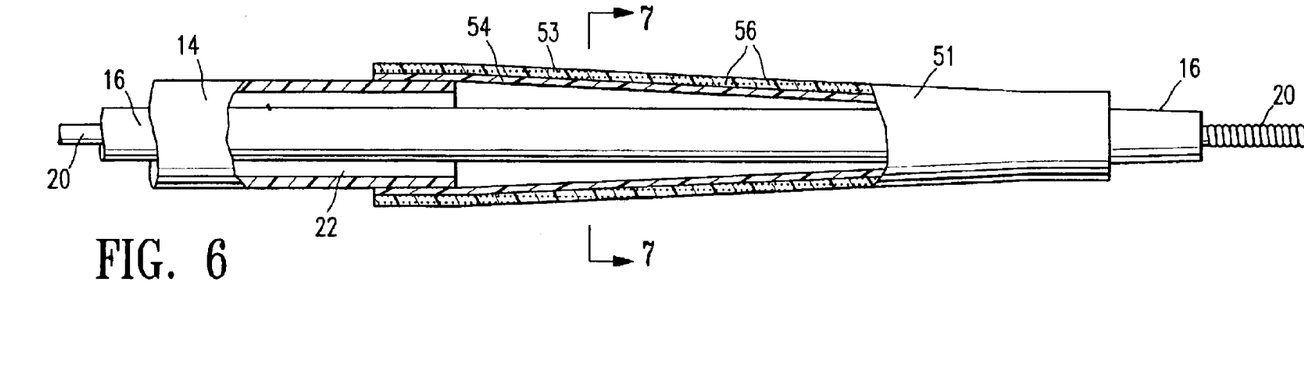
FIG. 6 is a longitudinal cross section of a distal end of an alternative embodiment of a balloon catheter that embodies features of the invention, having a balloon with a first layer impregnated with a polymer and a second layer bonded thereto.

FIG. 6 illustrates another embodiment, having balloon 51 comprising impregnated ePTFE layer 53 and including a second layer 54 bonded to the ePTFE layer 53. Second layer 54 is preferably formed of a polymer selected from the group consisting of a diene polymer, a polyurethane such as Tecoflex EG80A available from Thermedics Inc., Estane (a polyester based polyurethane) available from BF Goodrich, and HT-7 available from Apex Medical, and such as a silicone-polyurethane copolymer such as Pursil AL 575. FIG. 7 illustrates a transverse cross section of the balloon catheter of FIG. 6, taken along line 7—7. The second layer 54 is similar to layer 34 of the embodiment of FIG. 1. Thus, in one embodiment, the second layer 54 is formed of the diene polymer mixed with a bonding promoter which covalently bonds with unsaturation of the diene polymer of the second layer 54, for example by vulcanizing the diene polymer of the second layer, and hydrogen-bonds to the diene (e.g., the vulcanized diene) impregnated in the ePTFE layer 53. Preferably, the vulcanized or otherwise modified diene second layer 54 is heat fusion bonded to the ePTFE layer 53 impregnated with vulcanized or otherwise modified diene, using a method such as the method discussed above in relation to the embodiment of FIG. 1. The second layer 54 can be vulcanized with or otherwise coupled to the bonding promoter mixed therewith prior to being bonded to the ePTFE layer 53. Alternatively, the diene of the second layer 54 and the diene impregnated in the ePTFE first layer 53 can be vulcanized/coupled to the respective bonding promoter during the bonding together of layers 53 and 54. Thus, the diene polymer impregnated in the ePTFE is a bondable material allowing the layers 53 and 34 to fusion bond together. Specifically, the diene or modified/vulcanized diene impregnated in the ePTFE bonds as for example by hydrogen-bonding to the polar functionality of the bonding promoter coupled to the diene forming the second layer 54. As discussed above in relation to the embodiment of FIG. 1, in one embodiment (not shown), the diene layer 54 does not extend the entire length of the ePTFE layer 53, so that one or both end sections of the ePTFE layer 53 are bonded directly to the catheter shaft.

To the extent not previously discussed herein, the various catheter components may be formed and joined by conventional materials and methods. For example, inner tubular member 16 and outer tubular member 14 can be formed by conventional techniques, such as by extruding and necking materials found useful in intravascular catheters such a polyethylene, polyvinyl chloride, polyesters, polyamides, polyimides, polyurethanes, and composite materials.

The dimensions of catheter 10 are determined largely by the size of the balloon and guidewires to be employed, catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), the wall thickness of the outer tubular member 14 can vary from about 0.002 to about 0.008 inch (0.0051 to 0.02 cm), typically about 0.002 to 0.005 inch (0.005 to 0.013 cm). The inner tubular member 16 typically has an inner diameter of about 0.01 to about 0.018 inch(0.025 to 0.046 cm), usually about 0.016 inch (0.04 cm), and wall thickness of 0.002 to 0.008 inch (0.005 to 0.02 cm). The overall length of the catheter 10 may range from about 100 to about 150 cm, and is typically about 135 cm. Preferably, balloon 24 may have a length about 0.5 cm to about 4 cm and typically about 2 cm, and an inflated working diameter of about 1 to about 8 mm, and in a preferred embodiment, an uninflated diameter of not greater than about 1.3 mm. The thickness of the ePTFE first layer 33, 53 is about 0.001 inch to about 0.006 inch, preferably about 0.002 inch to about 0.004 inch, and the thickness of the second layer 34, 54 is about 0.001 inch to about 0.006 inch, preferably about 0.002 inch to about 0.004 inch.

The following examples more specifically illustrate various embodiments of the invention.

EXAMPLE I

Catheter balloons were prepared having a first layer of ePTFE with a plasma polymerized acrylic acid functionality (i.e., bondable material), and a second layer of a diene polymer and AMBT (i.e., a bonding promoter), as follows. 30 grams of Kraton 1611K styrene-isoprene-styrene block copolymer was mixed in 166 grams of THF, and to this mixture was added 0.92 grams of 6-amino 2-mercaptobenzothiazole (AMBT) from Aldrich. The solution was put on an agitator for 12 hours to ensure the formation of a uniformly dissolved solution. A Teflon coated mandrel having an outer diameter of about 0.026 inches was dip coated with the solution, and dried, and the resulting coating was removed from the mandrel, to produce a tube formed of the diene-AMBT mixture having an inner diameter of about 0.026 inch and an outer diameter of about 0.032 inch. The length of the diene-AMBT tube was trimmed to about 2 inches, and the diene-AMBT tube was placed over a balloon catheter shaft in preparation for attaching to an outer layer of ePTFE.

A tube of ePTFE was provided with a plasma polymerized acrylic acid functionality on an inner surface thereof, as described in copending U.S. patent application Ser. No. 09/827,887, incorporated by reference above. The ePTFE tube was placed over the diene-AMBT tube so that the ends of the ePTFE tube fully cover the diene-AMBT tube. A 0.091 inch outer diameter Teflon protective sheath was placed of the ePTFE tube, and the assembly placed within a balloon crimping device at a temperature of about 270° F. The catheter was pressurized with air to a pressure of about 20 psi and maintained at the elevated temperature for about 20 seconds, thereby bonding the ePTFE outer layer to the diene inner layer. The resulting balloons exhibited acceptable adhesion between the diene layer and the ePTFE layer during inflation and fatigue testing.

Alternatively, the diene-AMBT tubes were made using a melt extrusion process as follows. 1000 grams of Kraton were dried at about 120° F. for 3 hours and then mixed with 0.5 grams of mineral oil, and tumbled for 15 minutes. 20 grams of AMBT powder was added and the mixture tumbled for another 15 minutes. The Kraton-AMBT was then extruded using a single screw extruder at a temperatures within the various extrusion zones of about 250° F. to about 335° F. The cross head adapter and the die were set at a temperature of about 375° F. Tubing having an inner diameter of about 0.028 inch and an outer diameter of about 0.034 inch was extruded using an annular extrusion die with a 0.062 inch die size and a 0.046 mandrel. The tubing exiting the die was quenched in water at room temperature. The thus formed extruded diene-AMBT tube was bonded to the ePTFE layer as set forth above. The resulting balloons exhibited acceptable adhesion between the diene layer and the ePTFE layer during inflation and fatigue testing.

EXAMPLE II

Catheter balloons were prepared having a first layer of ePTFE impregnated with a diene-AMBT mixture (i.e., a bondable material), and a second layer of a diene polymer and AMBT (i.e., a bonding promoter), as follows. Diene-AMBT tubes were made using the dip coat method set forth above in Example I. A portion of the Kraton/THF/AMBT solution prepared was taken and diluted with THF in a 1:1 ratio to produce a solution having about 7.5% by weight of Kraton dissolved in THF. A 0.034 inch Teflon mandrel wet with the Kraton/THF/AMBT solution was slid into the inner lumen of a ePTFE tube, to expose the ePTFE tube to the solution. Uniform coating was produced by manually pressing the ePTFE tube along the entire length onto the mandrel to ensure good contact. The mandrel was removed and dry nitrogen at less than 20 psi was blown through the inner lumen of the ePTFE tube to evaporate the solvent. The Kraton/AMBT mixture is believed to form an interpenetrating network through the pores of the ePTFE due to the porous nature of the ePTFE, leading to a mechanical bond between the ePTFE and the Kraton/AMBT mixture. The thus impregnated ePTFE tube was bonded to the diene inner layer as set forth in Example 1. The resulting balloons exhibited acceptable adhesion between the diene layer and the ePTFE layer during inflation and fatigue testing.

While the present invention is described herein in terms of certain preferred embodiments, various modifications and improvements may be made to the invention without departing from the scope thereof. For example, in the embodiment illustrated in FIG. 1, the catheter is over-the-wire stent delivery catheter. However, one of skill in the art will readily recognize that other types of intravascular catheters may be used, such as rapid exchange dilatation catheters having a distal guidewire port and a proximal guidewire port and a short guidewire lumen extending between the proximal and distal guidewire ports in a distal section of the catheter. Additionally, although discussed in terms of a balloon for a catheter, a variety of expandable medical devices or components thereof may be made according the invention, including a cover for a stent, and a vascular graft. Moreover, although discussed in terms of a preferred low tensile set silicone-polyurethane or diene, it should be understood that silicone-polyurethanes and dienes having higher tensile sets can be used if desired. Although individual features of one embodiment of the invention may be discussed herein or shown in the drawings of one embodiment and not in other embodiments, it should be apparent that individual features of one embodiment may be combined with one or more features of another embodiment or features from a plurality of embodiments.

What is claimed:

1. A balloon catheter, comprising:
   a) an elongated shaft having a proximal end, a distal end, and an inflation lumen; and
   b) a balloon having a first layer formed of a porous polymeric material with a coating of an elastomeric polymeric material on a surface of the first layer, and with the elastomeric polymeric material impregnating the porous polymeric material of the first layer; and
   a second layer heat fusion bonded to the first layer and formed of a polymeric material compatible with, and different than, the elastomeric polymeric material of the first layer so that the polymeric material forming the second layer forms a heat fusion bond to the elastomeric polymeric material of the first layer to thereby fusion bond the first and second layers together without an adhesive between said first layer and said second layer, the second layer having a radial tensile set of about 0% to about 10% based on a radial expansion of at least about 300% of an initial diameter.

2. The balloon catheter of claim 1 wherein the balloon has a radial tensile set of about 1% to about 20% based on a radial expansion of at least about 300%.

3. The balloon catheter of claim 1 wherein the second layer radial tensile set is about 1% to about 5%.

4. The balloon catheter of claim 1 wherein the second layer material is an aliphatic ether urethane cosiloxane silicone-polyurethane copolymer.

5. The balloon catheter of claim 4 wherein the balloon has a radial tensile set of about 1% to about 10% based on a radial expansion of at least about 300%.

6. The balloon catheter of claim 4 wherein the second layer has an axial tensile set of about 1% to about 5% based on an axial expansion of at least about 300%.

7. The balloon catheter of claim 1 wherein the porous polymeric material of the first layer is expanded polytetrafluoroethylene.

8. The balloon catheter of claim 1 wherein the first layer comprises expanded polytetrafluoroethylene and has a plasma polymerized functionality bonded to at least a section of the first layer.

9. The balloon of claim 1 wherein the polymeric material forming the second layer has an elongation of greater than 400%.

10. The balloon of claim 9 wherein the polymeric material forming the second layer has a tensile strength of about 3000 psi to about 6500 psi.

11. The balloon catheter of claim 1 wherein the second layer is shorter than the first layer in a deflated configuration so that the first layer has proximal and distal end sections impregnated with the elastomeric polymeric material which have an inner surface extending onto the shaft beyond the second layer.

12. A balloon for a catheter, comprising:
 a) a first layer formed of expanded polytetrafluoroethylene impregnated with a first elastomeric polymer; and
 b) a second layer bonded to the first layer and formed of a second elastomeric polymer which is different from the first elastomeric polymer impregnating the first layer, so that the second elastomeric polymer forming the second layer is fusion bonded to the first elastomeric polymer impregnating the expanded polytetrafluoroethylene to thereby fusion bond the first and second layers together without an adhesive.

13. A balloon for a catheter, comprising:
 a first tube layer formed of expanded polytetrafluoroethylene impregnated with a low tensile set elastomeric polymer selected from the group consisting of a silicone-polyurethane copolymer, an isoprene, and a diene polymer, and a second tube layer formed of a low tensile set elastomeric polymer which is different than the polymer impregnating the expanded polytetrafluoroethylene, so that the polymer forming the second layer is fusion bonded to the polymer impregnating the expanded polytetrafluoroethylene to thereby fusion bond the first and second layers together without an adhesive, and the second layer is shorter than the first layer in a deflated configuration so that the first layer has an end section impregnated with the elastomeric polymeric material which has an inner surface extending beyond the second layer.

14. The balloon of claim 13 wherein the low tensile set polymer of the first tube layer is selected from the group consisting of the isoprene and the diene polymer, and the polymer of the second tube layer is mixed with a bonding promoter which is covalently bonded to the polymer of the second tube layer and bonded to the isoprene or diene polymer impregnated in the expanded polytetrafluoroethylene.

15. The balloon of claim 13 wherein the low tensile set polymer of the first tube layer is selected from the group consisting of the isoprene and the diene polymer, and includes a bonding promoter mixed with and covalently bonded to the polymer impregnated in the expanded polytetrafluoroethylene.

16. The balloon of claim 15 wherein the isoprene or diene polymer of the second tube layer is mixed with and covalently bonded to a bonding promoter so that the polymer-bonding promoter mixture of the second tube layer is bonded to the polymer-bonding promoter mixture impregnated in the expanded polytetrafluoroethylene.

17. The balloon of claim 16 wherein the bonding promoter of the second tube layer is selected from the group consisting of an aromatic thiol with an amine or carboxylic acid functionality, a thiuram disulfide, a mercapto amine, a mercapto epoxide, dansyl chloride, and thionin acetate.

* * * * *